United States Patent
Chiang et al.

(10) Patent No.: US 10,398,647 B2
(45) Date of Patent: Sep. 3, 2019

(54) HYDROGEL COMPOSITIONS AND DRUG DELIVERY SYSTEMS COMPRISING THE SAME

(71) Applicant: Industrial Technology Research Institute, Chutung, Hsinchu (TW)

(72) Inventors: Wen-Hsuan Chiang, Toufen (TW); Yu-Wen Lo, New Taipei (TW); Felice Cheng, Zhubei (TW); Maggie Lu, Zhudong Township, Hsinchu County (TW); Ya-Ling Chiu, Hsinchu (TW)

(73) Assignee: INDUSTRIAL TECHNOLOGY RESEARCH INSTITUTE, Hsinchu (TW)

( * ) Notice: Subject to any disclaimer, the term of this patent is extended or adjusted under 35 U.S.C. 154(b) by 0 days.

(21) Appl. No.: 15/788,920

(22) Filed: Oct. 20, 2017

(65) Prior Publication Data

US 2018/0110731 A1    Apr. 26, 2018

Related U.S. Application Data

(60) Provisional application No. 62/411,065, filed on Oct. 21, 2016.

(51) Int. Cl.
| | |
|---|---|
| *A61K 9/06* | (2006.01) |
| *A61K 47/10* | (2017.01) |
| *A61K 47/34* | (2017.01) |
| *A61K 31/704* | (2006.01) |
| *A61K 38/38* | (2006.01) |
| *A61K 38/17* | (2006.01) |
| *C07K 16/32* | (2006.01) |
| *A61K 39/395* | (2006.01) |
| *A61K 38/26* | (2006.01) |
| *A61K 33/30* | (2006.01) |
| *A61K 47/42* | (2017.01) |
| *A61K 39/00* | (2006.01) |
| *A61K 9/00* | (2006.01) |

(52) U.S. Cl.
CPC .............. *A61K 9/06* (2013.01); *A61K 31/704* (2013.01); *A61K 33/30* (2013.01); *A61K 38/1793* (2013.01); *A61K 38/26* (2013.01); *A61K 38/385* (2013.01); *A61K 39/39541* (2013.01); *A61K 39/39558* (2013.01); *A61K 47/10* (2013.01); *A61K 47/34* (2013.01); *A61K 47/42* (2013.01); *C07K 16/32* (2013.01); *A61K 9/0019* (2013.01); *A61K 9/0024* (2013.01); *A61K 2039/505* (2013.01); *C07K 2317/24* (2013.01); *C07K 2317/94* (2013.01)

(58) Field of Classification Search
CPC .......... A61K 9/06; A61K 47/10; A61K 47/34; A61K 38/385; A61K 38/1793; A61K 31/704; A61K 33/30

See application file for complete search history.

(56) References Cited

U.S. PATENT DOCUMENTS

| | | |
|---|---|---|
| 5,066,490 A | 11/1991 | Neville, Jr. et al. |
| 8,124,757 B2 | 2/2012 | Song |
| 8,519,086 B2 | 8/2013 | Bowman et al. |
| 8,647,670 B2 | 2/2014 | Shu |
| 9,254,348 B2 | 2/2016 | Koh et al. |
| 2011/0286926 A1 | 11/2011 | Sinko et al. |
| 2015/0299285 A1 | 10/2015 | Dimarchi et al. |

FOREIGN PATENT DOCUMENTS

| | | |
|---|---|---|
| CA | 2 692 553 A | 1/2009 |
| CN | 104684546 A | 6/2015 |
| CN | 104815335 A | 8/2015 |
| EP | 2468310 A1 | 6/2012 |
| TW | 200626626 A | 8/2006 |
| TW | 201300131 A1 | 1/2013 |
| WO | WO 2013/100715 A1 | 7/2013 |

OTHER PUBLICATIONS

Kirchhof et al., "Diels-Alder hydrogels with enhanced stability: First step toward controlled release of bevacizumab", European Journal of Pharmaceutics and Biopharmaceutics, vol. 96, 2015, pp. 217-225.

Lee et al., "Injectable Biodegradable Hydrogels from Vitamin D-Functionalized Polycarbonates for the Delivery of Avastin with Enhanced Therapeutic Efficiency against Metastatic Colorectal Cancer", Biomacromolecules, vol. 16, 2015, pp. 465-475.

Lee et al., "Injectable Hydrogels from Triblock Copolymers of Vitamin E-Functionalized Polycarbonate and Poly(ethylene glycol) for Subcutaneous Delivery of Antibodies for Cancer Therapy", Advanced Functional Materials, vol. 24, 2014, pp. 1538-1550.

Phelps et al., "Maleimide Cross-Linked Bioactive PEG Hydrogel Exhibits Improved Reaction Kinetics and Cross-Linking for Cell Encapsulation and In Situ Delivery", Advanced Materials, vol. 24, 2012, pp. 64-70.

Purcell et al., "Incorporation of Sulfated Hyaluronic Acid Macromers into Degradable Hydrogel Scaffolds for Sustained Molecule Delivery", Biomater Science, 2014, pp. 693-702.

Ren et al., "Injectable enzymatically crosslinked hydrogels based on a poly(L-glutamic acid) graft copolymer", Polymer Chemistry, vol. 5, 2014, pp. 5069-5076.

Schweider et al., "Pharmacokinetics, biocompatibility and bioavailability of a controlled release monoclonal antibody formulation", Journal of Controlled Release, vol. 172, 2013, pp. 975-982.

(Continued)

*Primary Examiner* — Zohreh A Fay
(74) *Attorney, Agent, or Firm* — Birch, Stewart, Kolasch & Birch, LLP

(57) ABSTRACT

A hydrogel composition is provided. The hydrogel composition includes polyglutamic acid (PGA) containing maleimide groups, and polyethylene glycol (PEG) containing terminal thiol groups, wherein the hydrogel composition has a pH value ranging from 4.0 to 6.5. A drug delivery system is also provided. The drug delivery system includes the above-mentioned hydrogel composition, and a pharmaceutically active ingredient encapsulated in the hydrogel composition.

21 Claims, 2 Drawing Sheets

(56) References Cited

OTHER PUBLICATIONS

Xu et al., "Hyaluronidase-incorporated hyaluronic acid- tryamine hydrogel for the sustained release of trastuzumab", Journal of Controlled Release, vol. 216, 2015, pp. 47-55.
Xu et al., "Sustained release of avastin from polysaccharides cross-linked hydrogels for ocular drug delivery", International Journal of Biological Macromolecules, vol. 60, 2013, pp. 272-276.
Yan et al., "Injectable In Situ Self-Cross-Linking Hydrogels Based on Poly(L-glutamic acid) and Alginate for Cartilage Tissue Engineering", Biomacromolecules, vol. 15, 2014, pp. 4495-4508.
Yang et al., "Poly(glutamic acid) poly(ethylene glycol) hydrogels prepared by photoinduced polymerization: Synthesis, characterization, and preliminary release studies of protein drugs", Journal of Biomedical Materials Research, Photoinduced Polymerization of Hydrogels, 2002, pp. 14-21.
Yu et al., "Formulation on In Situ Chemically Cross-Linked Hydrogel Depots for Protein Release: From the Blob Model Perspective". Biomacromolecules, vol. 16, 2015, pp. 56-65.
Extended European Search Report for Application No. 17197628.5, dated Mar. 6, 2018.
Markland, P., et al, "A pH- and ionic strength-responsive polypeptide hydrogel: Synthesis, characterization, and preliminary protein release studies," Journal of Biomedical Materials Research, 1999, vol. 47, pp. 595-602.
Taiwanese Office Action for Appl. No. 106135658 dated Jul. 20, 2018.

HYDROGEL COMPOSITIONS AND DRUG DELIVERY SYSTEMS COMPRISING THE SAME

CROSS REFERENCE TO RELATED APPLICATIONS

This application claims the benefit of U.S. Provisional Application No. 62/411,065, filed on Oct. 21, 2016, the entirety of which is incorporated by reference herein.

TECHNICAL FIELD

The technical field relates to a novel hydrogel composition and a drug delivery system comprising the same.

BACKGROUND

Currently, a common drug delivery carrier cannot carry high-concentration drugs. However, the use of many antibody drugs requires relatively high doses to be efficient. Therefore, the controlled-release technology of antibody drugs is facing difficult problems. In the preparation of a general carrier, the use of an organic solvent is required. However, the organic solvent often results in the inactivation of proteins. In addition, it is difficult to maintain the integrity and stability of molecular structure and biological activity of drugs during the drug-release period.

Therefore, the development of a kind of a carrier which is capable of carrying high-concentration drugs and maintaining the integrity and stability of molecular structure and biological activity of the loaded drugs during the drug-release period is desirable.

SUMMARY

In accordance with one embodiment of the disclosure, a hydrogel composition is provided. The hydrogel composition comprises polyglutamic acid (PGA) containing maleimide groups, and polyethylene glycol (PEG) containing terminal thiol groups. Specifically, the hydrogel composition has a pH value ranging from about 4.0 to about 6.5.

In accordance with another embodiment of the disclosure, a drug delivery system is provided. The drug delivery system comprises the above-mentioned hydrogel composition, and a pharmaceutically active ingredient encapsulated in the hydrogel composition.

A detailed description is given in the following embodiments with reference to the accompanying drawings.

BRIEF DESCRIPTION OF DRAWINGS

The present disclosure can be more fully understood by reading the subsequent detailed description and examples with references made to the accompanying drawings, wherein.

DETAILED DESCRIPTION

Figure 1:
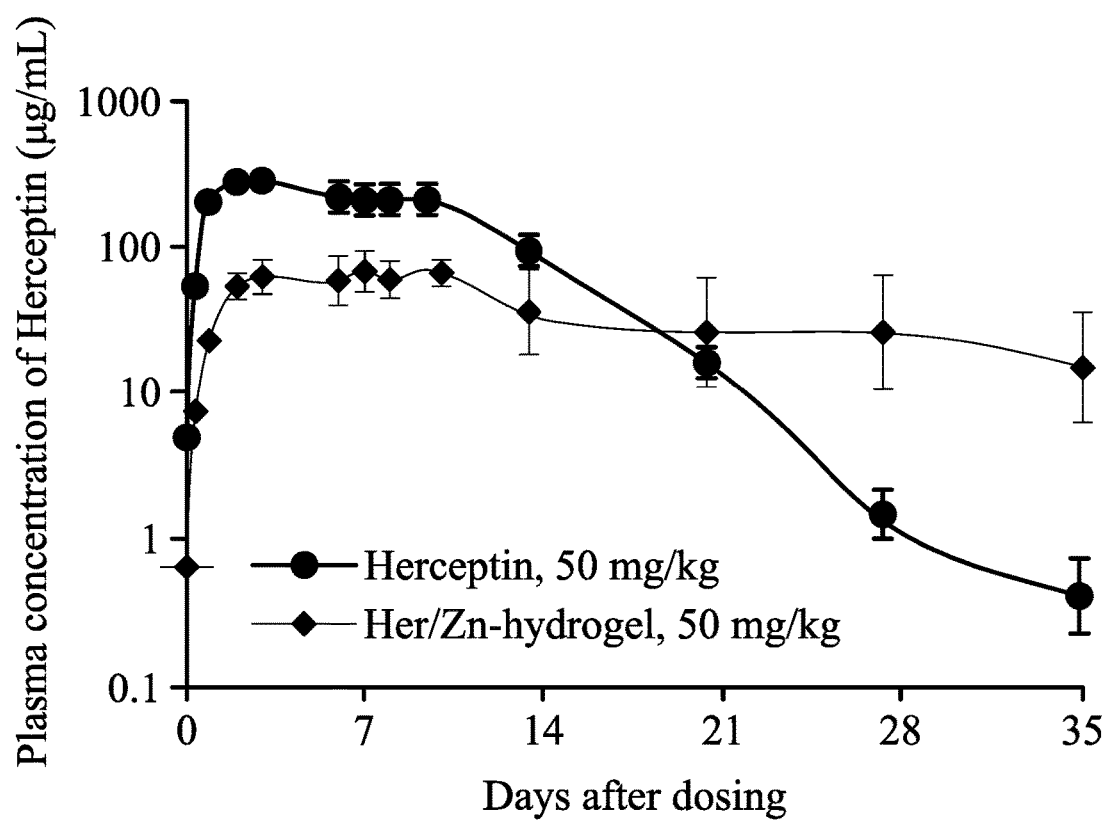
FIG. 1 is a figure showing the serum concentration-time profiles according to an embodiment of the disclosure.

In the following detailed description, for the purposes of explanation, numerous specific details are set forth in order to provide a thorough understanding of the disclosed embodiments. It will be apparent, however, that one or more embodiments may be practiced without these specific details. In other instances, well-known structures and devices are shown schematically in order to simplify the drawing.

In accordance with one embodiment of the disclosure, a hydrogel composition is provided. The hydrogel composition comprises polyglutamic acid (PGA) containing maleimide groups, and polyethylene glycol (PEG) containing terminal thiol groups. Specifically, the hydrogel composition has a pH value ranging from about 4.0 to about 6.5.

In some embodiments, the polyglutamic acid (PGA) containing maleimide groups (e.g.,

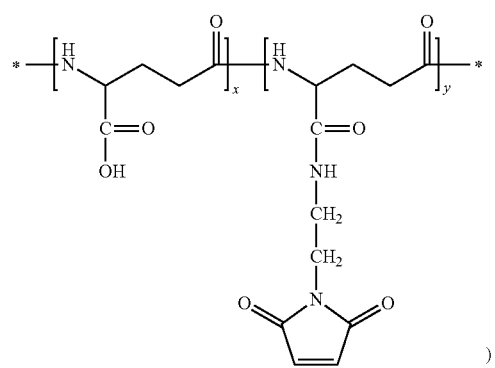

) has a molecular weight ranging from about 10 kDa to about 1,000 kDa.

In some embodiments, the polyglutamic acid (PGA) containing maleimide groups has a grafting ratio ranging from about 5% to about 40%.

In some embodiments, the polyglutamic acid (PGA) containing maleimide groups has a concentration ranging from about 0.75 wt % to about 10 wt % in the hydrogel composition.

In some embodiments, the polyglutamic acid (PGA) containing maleimide groups is free of thiol groups.

In some embodiments, the polyethylene glycol (PEG) containing terminal thiol groups has a molecular weight ranging from about 2 kDa to about 20 kDa.

In some embodiments, the polyethylene glycol (PEG) containing terminal thiol groups has a concentration ranging from about 0.75 wt % to about 10 wt % in the hydrogel composition.

In some embodiments, the polyethylene glycol (PEG) containing terminal thiol groups may be 4-arm type (e.g.,

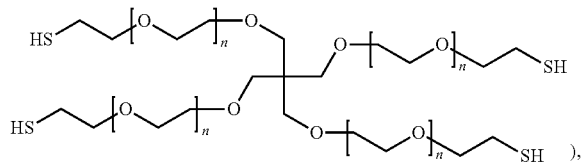

8-arm type or Y-shape.

In some embodiments, the polyethylene glycol (PEG) containing terminal thiol groups is free of maleimide groups.

In some embodiments, the polyethylene glycol (PEG) containing terminal thiol groups and the polyglutamic acid (PGA) containing maleimide groups have a molar ratio of the thiol group to the maleimide group ranging from about 0.2 to about 5.0.

In some embodiments, the polyethylene glycol (PEG) containing terminal thiol groups and the polyglutamic acid (PGA) containing maleimide groups have a molar ratio of the thiol group to the maleimide group ranging from about 1.0 to about 1.5.

In accordance with another embodiment of the disclosure, a drug delivery system is provided. The drug delivery system comprises a hydrogel composition, and a pharmaceutically active ingredient encapsulated in the hydrogel composition.

In some embodiments, the hydrogel composition may comprise polyglutamic acid (PGA) containing maleimide groups, and polyethylene glycol (PEG) containing terminal thiol groups. The hydrogel composition has a pH value ranging from about 4.0 to about 6.5.

In some embodiments, the polyglutamic acid (PGA) containing maleimide groups has a molecular weight ranging from about 10 kDa to about 1,000 kDa.

In some embodiments, the polyglutamic acid (PGA) containing maleimide groups has a grafting ratio ranging from about 5% to about 40%.

In some embodiments, the polyglutamic acid (PGA) containing maleimide groups has a concentration ranging from about 0.75 wt % to about 10 wt % in the hydrogel composition.

In some embodiments, the polyglutamic acid (PGA) containing maleimide groups is free of thiol groups.

In some embodiments, the polyethylene glycol (PEG) containing terminal thiol groups has a molecular weight ranging from about 2 kDa to about 20 kDa.

In some embodiments, the polyethylene glycol (PEG) containing terminal thiol groups has a concentration ranging from about 0.75 wt % to about 10 wt % in the hydrogel composition.

In some embodiments, the polyethylene glycol (PEG) containing terminal thiol groups may be 4-arm type, 8-arm type or Y-shape.

In some embodiments, the polyethylene glycol (PEG) containing terminal thiol groups is free of maleimide groups.

In some embodiments, the polyethylene glycol (PEG) containing terminal thiol groups and the polyglutamic acid (PGA) containing maleimide groups have a molar ratio of the thiol group to the maleimide group ranging from about 0.2 to about 5.0.

In some embodiments, the polyethylene glycol (PEG) containing terminal thiol groups and the polyglutamic acid (PGA) containing maleimide groups have a molar ratio of the thiol group to the maleimide group ranging from about 1.0 to about 1.5.

In some embodiments, the pharmaceutically active ingredient may be selected from a group consisting of peptides, proteins, growth factors, hormones, antibodies, and hydrophilic or hydrophobic small molecules.

In some embodiments, the pharmaceutically active ingredient may be selected from a group consisting of intact antibodies and antibody fragments.

In some embodiments, the pharmaceutically active ingredient may be selected from a group consisting of murine antibodies, chimeric antibodies, humanized antibodies, and human antibodies.

In some embodiments, the pharmaceutically active ingredient may be selected from a group consisting of antineoplastic agents, antipsychotics, analgesics and antibiotics.

In some embodiments, the pharmaceutically active ingredient may be further associated with a polymer, metal, charged compounds or charged particles to form a complex thereof.

In some embodiments, the polymer may comprise polyglutamic acid (PGA) or other suitable polymers such as hyaluronic acid, chitosan, alginate or dextran.

In some embodiments, the metal may comprise zinc or other suitable metals such as calcium, magnesium or iron.

In some embodiments, the complex has a size ranging from about 10 nm to about 100 μm.

In some embodiments, the pharmaceutically active ingredient or the complex has a concentration ranging from about 1 mg/mL to about 300 mg/mL.

Poly(γ-glutamic acid) (γ-PGA) is a high-molecular-weight polypeptide composed of γ-linked glutamic acid units and α-carboxylate side chain. γ-PGA is ideal biomaterials able to be applied to fabricate functionalized hydrogel systems because of its many advantages such us nontoxicity, hydrophilicity, biodegradability, and avoiding antigenicity or immunogenicity. In addition, the abundant carboxyl groups on the γ-PGA chains could be chemically modified, and associated with soluble antibody molecules upon electrostatic interaction.

Poly(ethylene glycol) (PEG) as the uncharged hydrophilic segments have been extensively employed to construct the chemically or physically cross-linked hydrogel systems due to its biocompatibility. PEG-based hydrogels have been used as cell scaffolds, adhesive medical applications, and delivery vehicles. Particularly, the ability to regulate the crosslinking density provides the flexibility and tailorability to PEG-based hydrogels for cell encapsulation and tissue growth.

In the disclosure, in order to achieve high drug loading content (beyond 150 mg/mL) and long-lasting sustained drug release (over 21 days), the subcutaneously injectable and in situ forming hydrogel systems composed of γ-PGA and 4-arm PEG are developed. The γ-PGA is partially modified by N-(2-aminoethyl) maleimide upon the aminolization. The resulting maleimide-containing γ-PGA (γ-PGA-MA) is mixed with 4-arm PEG-SH in aqueous solutions. Through the pH-sensitive Michael addition reaction between maleimide groups and thiol groups, the chemically cross-linked hydrogels are formed.

EXAMPLES/COMPARATIVE EXAMPLES

Example 1

Preparation of the Hydrogel Composition (1)

First, 0.002 g of polyglutamic acid (PGA) containing maleimide groups (Mw: 1,000 kDa, DS (grafting ratio): 31.6%) was dissolved in 50 μL of PBS to prepare a first solution (concentration: 4.0 wt %). Next, 0.002 g of polyethylene glycol (PEG) containing thiol groups (Mw: 5 kDa, 4-arm type) was dissolved in 50 μL of PBS to prepare a second solution (concentration: 4.0 wt %). The first solution and the second solution were then blended at an equal volume (50 μL) to prepare a hydrogel. In this preparation, the molar ratio of the thiol groups to the maleimide groups was 0.4, and the pH of the blending solution was 5.5. By visual confirmation, the gelation was successful.

Example 2

Preparation of the Hydrogel Composition (2)

First, 0.002 g of polyglutamic acid (PGA) containing maleimide groups (Mw: 1,000 kDa, DS (grafting ratio): 31.6%) was dissolved in 50 μL of PBS to prepare a first solution (concentration: 4.0 wt %). Next, 0.004 g of polyethylene glycol (PEG) containing thiol groups (Mw: 5 kDa, 4-arm type) was dissolved in 50 μL of PBS to prepare a second solution (concentration: 8.0 wt %). The first solution and the second solution were then blended at an equal volume (50 μL) to prepare a hydrogel. In this preparation, the molar ratio of the thiol groups to the maleimide groups was 0.8, and the pH of the blending solution was 5.5. By visual confirmation, the gelation was successful.

Example 3

Preparation of the Hydrogel Composition (3)

First, 0.002 g of polyglutamic acid (PGA) containing maleimide groups (Mw: 1,000 kDa, DS (grafting ratio): 31.6%) was dissolved in 50 μL of PBS to prepare a first solution (concentration: 4.0 wt %). Next, 0.005 g of polyethylene glycol (PEG) containing thiol groups (Mw: 5 kDa, 4-arm type) was dissolved in 50 μL of PBS to prepare a second solution (concentration: 10 wt %). The first solution and the second solution were then blended at an equal volume (50 μL) to prepare a hydrogel. In this preparation, the molar ratio of the thiol groups to the maleimide groups was 1.0, and the pH of the blending solution was 5.5. By visual confirmation, the gelation was successful.

Example 4

Preparation of the Hydrogel Composition (4)

First, 0.001 g of polyglutamic acid (PGA) containing maleimide groups (Mw: 1,000 kDa, DS (grafting ratio): 31.6%) was dissolved in 50 μL of PBS to prepare a first solution (concentration: 2.0 wt %, pH: 4.0). Next, 0.002 g of polyethylene glycol (PEG) containing thiol groups (Mw: 5 kDa, 4-arm type) was dissolved in 50 μL of PBS to prepare a second solution (concentration: 4.0 wt %, pH: 7.2). The first solution and the second solution were then blended at an equal volume (50 μL) to prepare a hydrogel. In this preparation, the molar ratio of the thiol groups to the maleimide groups was 0.8, and the pH of the blending solution was 5.6. By visual confirmation, the gelation was successful and took 12 minutes.

Example 5

Preparation of the Hydrogel Composition (5)

First, 0.001 g of polyglutamic acid (PGA) containing maleimide groups (Mw: 1,000 kDa, DS (grafting ratio): 31.6%) was dissolved in 50 μL of PBS to prepare a first solution (concentration: 2.0 wt %, pH: 4.0). Next, 0.002 g of polyethylene glycol (PEG) containing thiol groups (Mw: 5 kDa, 4-arm type) was dissolved in 50 μL of deionized water to prepare a second solution (concentration: 4.0 wt %, pH: 4.4). The first solution and the second solution were then blended at an equal volume (50 μL) to prepare a hydrogel. In this preparation, the molar ratio of the thiol groups to the maleimide groups was 0.8, and the pH of the blending solution was 4.3. By visual confirmation, the gelation was successful and took 20 minutes.

Example 6

Preparation of the Hydrogel Composition (6)

First, 0.001 g of polyglutamic acid (PGA) containing maleimide groups (Mw: 1,000 kDa, DS (grafting ratio): 31.6%) was dissolved in 50 μL of deionized water to prepare a first solution (concentration: 2.0 wt %, pH: 3.9). Next, 0.002 g of polyethylene glycol (PEG) containing thiol groups (Mw: 5 kDa, 4-arm type) was dissolved in 50 μL of deionized water to prepare a second solution (concentration: 4.0 wt %, pH: 4.4). The first solution and the second solution were then blended at an equal volume (50 μL) to prepare a hydrogel. In this preparation, the molar ratio of the thiol groups to the maleimide groups was 0.8, and the pH of the blending solution was 4.1. By visual confirmation, the gelation was successful and took 6 hours more.

Example 7

Preparation of the Hydrogel Composition (7)

First, 0.002 g of polyglutamic acid (PGA) containing maleimide groups (Mw: 1,000 kDa, DS (grafting ratio): 31.6%) was dissolved in 50 μL of PBS to prepare a first solution (concentration: 4.0 wt %, pH: 3.9). Next, 0.002 g of polyethylene glycol (PEG) containing thiol groups (Mw: 5 kDa, 4-arm type) was dissolved in 50 μL of deionized water to prepare a second solution (concentration: 4.0 wt %, pH: 4.4). The first solution and the second solution were then blended at an equal volume (50 μL) to prepare a hydrogel. In this preparation, the molar ratio of the thiol groups to the maleimide groups was 0.4, and the pH of the blending solution was 4.2. By visual confirmation, the gelation was successful and took 10 minutes.

Example 8

Preparation of the Hydrogel Composition (8)

First, 0.001 g of polyglutamic acid (PGA) containing maleimide groups (Mw: 1,000 kDa, DS (grafting ratio): 31.6%) was dissolved in 50 μL of PBS to prepare a first solution (concentration: 2.0 wt %, pH: 4.0). Next, 0.002 g of polyethylene glycol (PEG) containing thiol groups (Mw: 10 kDa, 4-arm type) was dissolved in 50 μL of PBS to prepare a second solution (concentration: 4.0 wt %, pH: 7.2). The first solution and the second solution were then blended at an equal volume (50 μL) to prepare a hydrogel. In this preparation, the molar ratio of the thiol groups to the maleimide groups was 0.4, and the pH of the blending solution was 5.6. By visual confirmation, the gelation was successful and took 2-3 minutes.

Example 9

Preparation of the Hydrogel Composition (9)

First, 0.001 g of polyglutamic acid (PGA) containing maleimide groups (Mw: 1,000 kDa, DS (grafting ratio): 31.6%) was dissolved in 50 μL of PBS to prepare a first solution (concentration: 2.0 wt %, pH: 4.0). Next, 0.0015 g of polyethylene glycol (PEG) containing thiol groups (Mw: 10 kDa, 4-arm type) was dissolved in 50 μL of PBS to prepare a second solution (concentration: 3 wt %, pH: 7.2). The first solution and the second solution were then blended at an equal volume (50 μL) to prepare a hydrogel. In this preparation, the molar ratio of the thiol groups to the maleimide groups was 0.3, and the pH of the blending solution was 5.6. By visual confirmation, the gelation was successful and took 6-8 minutes.

Example 10

Preparation of the Hydrogel Composition (10)

First, 0.002 g of polyglutamic acid (PGA) containing maleimide groups (Mw: 200-400 kDa, DS (grafting ratio): 11.5%) was dissolved in 50 μL of 0.9% NaCl solution to prepare a first solution (concentration: 4.0 wt %, pH: 4.2). Next, 0.004 g of polyethylene glycol (PEG) containing thiol groups (Mw: 5 kDa, 4-arm type) was dissolved in 50 μL of 0.9% NaCl solution to prepare a second solution (concentration: 8.0 wt %, pH: 5.5). The first solution and the second solution were then blended at an equal volume (50 μL) to prepare a hydrogel. In this preparation, the molar ratio of the thiol groups to the maleimide groups was 2.0, and the pH of the blending solution was 4.9. By visual confirmation, the gelation was successful and took less than 5 minutes.

Example 11

Preparation of the Hydrogel Composition (11)

First, 0.002 g of polyglutamic acid (PGA) containing maleimide groups (Mw: 200-400 kDa, DS (grafting ratio): 11.5%) was dissolved in 50 μL of 0.9% NaCl solution to prepare a first solution (concentration: 4.0 wt %, pH: 4.2). Next, 0.006 g of polyethylene glycol (PEG) containing thiol groups (Mw: 5 kDa, 4-arm type) was dissolved in 50 μL of 0.9% NaCl solution to prepare a second solution (concentration: 12.0 wt %, pH: 5.5). The first solution and the second solution were then blended at an equal volume (50 μL) to prepare a hydrogel. In this preparation, the molar ratio of the thiol groups to the maleimide groups was 3.0, and the pH of the blending solution was 4.9. By visual confirmation, the gelation was successful and took less than 5 minutes.

Example 12

Preparation of the Hydrogel Composition (12)

First, 0.002 g of polyglutamic acid (PGA) containing maleimide groups (Mw: 200-400 kDa, DS (grafting ratio): 11.5%) was dissolved in 50 μL of 0.9% NaCl solution to prepare a first solution (concentration: 4.0 wt %, pH: 4.2). Next, 0.01 g of polyethylene glycol (PEG) containing thiol groups (Mw: 5 kDa, 4-arm type) was dissolved in 50 μL of 0.9% NaCl solution to prepare a second solution (concentration: 20 wt %, pH: 5.5). The first solution and the second solution were then blended at an equal volume (50 μL) to prepare a hydrogel. In this preparation, the molar ratio of the thiol groups to the maleimide groups was 5.0, and the pH of the blending solution was 4.9. By visual confirmation, the gelation was successful and took over one day.

Example 13

Preparation of the Hydrogel Composition (13)

First, 0.01 g of polyglutamic acid (PGA) containing maleimide groups (Mw: 200-400 kDa, DS (grafting ratio): 5.4%) was dissolved in 50 μL of 0.9% NaCl solution to prepare a first solution (concentration: 20 wt %, pH: 4.2). Next, 0.005 g of polyethylene glycol (PEG) containing thiol groups (Mw: 5 kDa, 4-arm type) was dissolved in 50 μL of 0.9% NaCl solution to prepare a second solution (concentration: 10 wt %, pH: 5.5). The first solution and the second solution were then blended at an equal volume (50 μL) to prepare a hydrogel. In this preparation, the molar ratio of the thiol groups to the maleimide groups was 1.0, and the pH of the blending solution was 4.9. By visual confirmation, the gelation was successful and took 2-3 minutes.

Example 14

Preparation of the Hydrogel Composition (14)

First, 0.01 g of polyglutamic acid (PGA) containing maleimide groups (Mw: 200-400 kDa, DS (grafting ratio): 11.5%) was dissolved in 50 μL of PBS to prepare a first solution (concentration: 20 wt %, pH: 4.2). Next, 0.01 g of polyethylene glycol (PEG) containing thiol groups (Mw: 5 kDa, 4-arm type) was dissolved in 50 μL of 0.9% NaCl solution to prepare a second solution (concentration: 20 wt %, pH: 5.5). The first solution and the second solution were then blended at an equal volume (50 μL) to prepare a hydrogel. In this preparation, the molar ratio of the thiol groups to the maleimide groups was 1.0, and the pH of the blending solution was 4.9. By visual confirmation, the gelation was successful and took 1-2 minutes.

Example 15

Preparation of the Drug Delivery System (1)

0.00106 g of Herceptin powder was dissolved in 0.9% NaCl solution to form a drug solution (concentration: 10.6 mg/mL). Next, 0.001 g of polyglutamic acid (PGA) containing maleimide groups (Mw: 1,000 kDa, DS (grafting ratio): 12.5%) was dissolved in 50 μL of the drug solution to prepare a first solution (concentration: 2.0 wt %). Next, 0.001 g of polyethylene glycol (PEG) containing thiol groups (Mw: 5 kDa, 4-arm type) was dissolved in 50 μL of the drug solution to prepare a second solution (concentration: 2.0 wt %). The first solution and the second solution were then blended at an equal volume (50 μL) to prepare a hydrogel. In this preparation, the molar ratio of the thiol groups to the maleimide groups was 0.89, and the pH of the blending solution was 6.0. By visual confirmation, the gelation was successful and took 4 minutes.

Example 16

Preparation of the Drug Delivery System (2)

0.00106 g of Herceptin powder was dissolved in 0.9% NaCl solution to form a drug solution (concentration: 10.6 mg/mL). Next, 0.001 g of polyglutamic acid (PGA) containing maleimide groups (Mw: 1,000 kDa, DS (grafting ratio): 12.5%) was dissolved in 50 μL of the drug solution to prepare a first solution (concentration: 2.0 wt %). Next, 0.00075 g of polyethylene glycol (PEG) containing thiol groups (Mw: 5 kDa, 4-arm type) was dissolved in 50 μL of the drug solution to prepare a second solution (concentration: 1.5 wt %). The first solution and the second solution were then blended at an equal volume (50 μL) to prepare a hydrogel. In this preparation, the molar ratio of the thiol groups to the maleimide groups was 0.67, and the pH of the blending solution was 6.0. By visual confirmation, the gelation was successful and took 5 minutes.

Example 17

Preparation of the Drug Delivery System (3)

0.00106 g of Herceptin powder was dissolved in 0.9% NaCl solution to form a drug solution (concentration: 10.6 mg/mL). Next, 0.0015 g of polyglutamic acid (PGA) containing maleimide groups (Mw: 1,000 kDa, DS (grafting ratio): 5.3%) was dissolved in 50 μL of the drug solution to prepare a first solution (concentration: 3.0 wt %). Next, 0.001 g of polyethylene glycol (PEG) containing thiol groups (Mw: 5 kDa, 4-arm type) was dissolved in 50 μL of the drug solution to prepare a second solution (concentration: 2.0 wt %). The first solution and the second solution were then blended at an equal volume (50 μL) to prepare a hydrogel. In this preparation, the molar ratio of the thiol groups to the maleimide groups was 1.33, and the pH of the blending solution was 6.0. By visual confirmation, the gelation was successful and took 5 minutes.

Example 18

Preparation of the Drug Delivery System (4)

0.00106 g of Herceptin powder was dissolved in 0.9% NaCl solution to form a drug solution (concentration: 10.6 mg/mL). Next, 0.0015 g of polyglutamic acid (PGA) containing maleimide groups (Mw: 1,000 kDa, DS (grafting ratio): 5.3%) was dissolved in 50 μL of the drug solution to prepare a first solution (concentration: 3.0 wt %). Next, 0.00075 g of polyethylene glycol (PEG) containing thiol groups (Mw: 5 kDa, 4-arm type) was dissolved in 50 μL of the drug solution to prepare a second solution (concentration: 1.5 wt %). The first solution and the second solution were then blended at an equal volume (50 μL) to prepare a hydrogel. In this preparation, the molar ratio of the thiol groups to the maleimide groups was 1.0, and the pH of the blending solution was 6.0. By visual confirmation, the gelation was successful and took 6 minutes.

Example 19

Preparation of the Drug Delivery System (5)

0.1 g of Herceptin powder was dissolved in deionized water and then dialyzed (MWCO: 10,000) against sodium chloride aqueous solution (0.9%) at 4° C. for 24 hours to form a drug solution. Next, the drug solution was centrifuged (4,000 g, 4° C.) and concentrated to 145.5 mg/mL. Next, 0.0015 g of polyglutamic acid (PGA) containing maleimide groups (Mw: 1,000 kDa, DS (grafting ratio): 5.3%) was dissolved in 50 μL of the drug solution to prepare a first solution (concentration: 3.0 wt %). Next, 0.001 g of polyethylene glycol (PEG) containing thiol groups (Mw: 5 kDa, 4-arm type) was dissolved in 50 μL of the drug solution to prepare a second solution (concentration: 2.0 wt %). The first solution and the second solution were then blended at an equal volume (50 μL) to prepare a hydrogel. In this preparation, the molar ratio of the thiol groups to the maleimide groups was 1.33, and the pH of the blending solution was 6.0. By visual confirmation, the gelation was successful and took 1 minute.

Example 20

Preparation of the Drug Delivery System (6)

0.1 g of Herceptin powder was dissolved in deionized water and then dialyzed (MWCO: 10,000) against sodium chloride aqueous solution (0.9%) at 4° C. for 24 hours to form a drug solution. Next, the drug solution was centrifuged (4,000 g, 4° C.) and concentrated to 145.5 mg/mL. Next, 0.0015 g of polyglutamic acid (PGA) containing maleimide groups (Mw: 1,000 kDa, DS (grafting ratio): 5.3%) was dissolved in 50 μL of the drug solution to prepare a first solution (concentration: 3.0 wt %). Next, 0.00075 g of polyethylene glycol (PEG) containing thiol groups (Mw: 5 kDa, 4-arm type) was dissolved in 50 μL of the drug solution to prepare a second solution (concentration: 1.5 wt %). The first solution and the second solution were then blended at an equal volume (50 μL) to prepare a hydrogel. In this preparation, the molar ratio of the thiol groups to the maleimide groups was 1.0, and the pH of the blending solution was 6.0. By visual confirmation, the gelation was successful and took 1 minute.

Example 21

Preparation of the Drug Delivery System (7)

0.1 g of Herceptin powder was dissolved in deionized water and then dialyzed (MWCO: 10,000) against sodium chloride aqueous solution (0.9%) at 4° C. for 24 hours to form a drug solution. Next, the drug solution was centrifuged (4,000 g, 4° C.) and concentrated to 145.5 mg/mL. Next, 0.00075 g of polyglutamic acid (PGA) containing maleimide groups (Mw: 1,000 kDa, DS (grafting ratio): 12.5%) was dissolved in 50 μL of the drug solution to prepare a first solution (concentration: 1.5 wt %). Next, 0.0006 g of polyethylene glycol (PEG) containing thiol groups (Mw: 5 kDa, 4-arm type) was dissolved in 50 μL of the drug solution to prepare a second solution (concentration: 1.2 wt %). The first solution and the second solution were then blended at an equal volume (50 μL) to prepare a hydrogel. In this preparation, the molar ratio of the thiol groups to the maleimide groups was 0.71, and the pH of the blending solution was 6.0. By visual confirmation, the gelation was successful and took 1 minute.

Example 22

Preparation of the Drug Delivery System (8)

0.1 g of Herceptin powder was dissolved in deionized water and then dialyzed (MWCO: 10,000) against sodium chloride aqueous solution (0.9%) at 4° C. for 24 hours to form a drug solution. Next, the drug solution was centrifuged (4,000 g, 4° C.) and concentrated to 128.6 mg/mL. Next, 0.00075 g of polyglutamic acid (PGA) containing maleimide groups (Mw: 200-400 kDa, DS (grafting ratio): 11.3%) was dissolved in 50 μL of the drug solution to prepare a first solution (concentration: 1.5 wt %). Next, 0.00075 g of polyethylene glycol (PEG) containing thiol groups (Mw: 5 kDa, 4-arm type) was dissolved in 50 μL of the drug solution to prepare a second solution (concentration: 1.5 wt %). The first solution and the second solution were then blended at an equal volume (50 μL) to prepare a hydrogel. In this preparation, the molar ratio of the thiol groups to the maleimide groups was 1.0, and the pH of the blending solution was 6.0. By visual confirmation, the gelation was successful and took 20 minutes.

Example 23

Preparation of the Drug Delivery System (9)

0.1 g of Herceptin powder was dissolved in deionized water and then dialyzed (MWCO: 10,000) against sodium chloride aqueous solution (0.9%) at 4° C. for 24 hours to form a drug solution. Next, the drug solution was centrifuged (4,000 g, 4° C.) and concentrated to 128.6 mg/mL. Next, 0.001 g of polyglutamic acid (PGA) containing maleimide groups (Mw: 200-400 kDa, DS (grafting ratio): 11.3%) was dissolved in 50 μL of the drug solution to prepare a first solution (concentration: 2.0 wt %). Next, 0.001 g of polyethylene glycol (PEG) containing thiol groups (Mw: 5 kDa, 4-arm type) was dissolved in 50 μL of the drug solution to prepare a second solution (concentration: 2.0 wt %). The first solution and the second solution were then blended at an equal volume (50 μL) to prepare a hydrogel. In this preparation, the molar ratio of the thiol groups to the maleimide groups was 1.0, and the pH of the blending solution was 6.0. By visual confirmation, the gelation was successful and took 10 minutes.

Example 24

Preparation of the Drug Delivery System (10)

0.1 g of Herceptin powder was dissolved in deionized water and then dialyzed (MWCO: 10,000) against sodium chloride aqueous solution (0.9%) at 4° C. for 24 hours to form a drug solution. Next, the drug solution was centrifuged (4,000 g, 4° C.) and concentrated to 128.6 mg/mL. Next, 0.0015 g of polyglutamic acid (PGA) containing maleimide groups (Mw: 200-400 kDa, DS (grafting ratio): 11.3%) was dissolved in 50 μL of the drug solution to prepare a first solution (concentration: 3.0 wt %). Next, 0.0015 g of polyethylene glycol (PEG) containing thiol groups (Mw: 5 kDa, 4-arm type) was dissolved in 50 μL of the drug solution to prepare a second solution (concentration: 3.0 wt %). The first solution and the second solution were then blended at an equal volume (50 μL) to prepare a hydrogel. In this preparation, the molar ratio of the thiol groups to the maleimide groups was 1.0, and the pH of the blending solution was 6.0. By visual confirmation, the gelation was successful and took 4 minutes.

Example 25

Preparation of the Drug Delivery System (11)

0.1 g of Herceptin powder was dissolved in deionized water and then dialyzed (MWCO: 10,000) against sodium chloride aqueous solution (0.9%) at 4° C. for 24 hours to form a drug solution. Next, the drug solution was centrifuged (4,000 g, 4° C.) and concentrated to 205 mg/mL. Next, 0.00075 g of polyglutamic acid (PGA) containing maleimide groups (Mw: 200-400 kDa, DS (grafting ratio): 11.3%) was dissolved in 50 μL of the drug solution to prepare a first solution (concentration: 1.5 wt %). Next, 0.00075 g of polyethylene glycol (PEG) containing thiol groups (Mw: 5 kDa, 4-arm type) was dissolved in 50 μL of the drug solution to prepare a second solution (concentration: 1.5 wt %). The first solution and the second solution were then blended at an equal volume (50 μL) to prepare a hydrogel. In this preparation, the molar ratio of the thiol groups to the maleimide groups was 1.0, and the pH of the blending solution was 6.0. By visual confirmation, the gelation was successful and took 15-17 minutes.

Example 26

Preparation of the Drug Delivery System (12)

0.1 g of Herceptin powder was dissolved in deionized water and then dialyzed (MWCO: 10,000) against sodium chloride aqueous solution (0.9%) at 4° C. for 24 hours to form a drug solution. Next, the drug solution was centrifuged (4,000 g, 4° C.) and concentrated to 205 mg/mL. Next, 0.001 g of polyglutamic acid (PGA) containing maleimide groups (Mw: 200-400 kDa, DS (grafting ratio): 11.3%) was dissolved in 50 μL of the drug solution to prepare a first solution (concentration: 2.0 wt %). Next, 0.001 g of polyethylene glycol (PEG) containing thiol groups (Mw: 5 kDa, 4-arm type) was dissolved in 50 μL of the drug solution to prepare a second solution (concentration: 2.0 wt %). The first solution and the second solution were then blended at an equal volume (50 μL) to prepare a hydrogel. In this preparation, the molar ratio of the thiol groups to the maleimide groups was 1.0, and the pH of the blending solution was 6.0. By visual confirmation, the gelation was successful and took 5-6 minutes.

Example 27

Preparation of the Drug Delivery System (13)

0.1 g of Herceptin powder was dissolved in deionized water and then dialyzed (MWCO: 10,000) against sodium chloride aqueous solution (0.9%) at 4° C. for 24 hours to form a drug solution. Next, the drug solution was centrifuged (4,000 g, 4° C.) and concentrated to 205 mg/mL. Next, 0.0015 g of polyglutamic acid (PGA) containing maleimide groups (Mw: 200-400 kDa, DS (grafting ratio): 11.3%) was dissolved in 50 μL of the drug solution to prepare a first solution (concentration: 3.0 wt %). Next, 0.0015 g of polyethylene glycol (PEG) containing thiol groups (Mw: 5 kDa, 4-arm type) was dissolved in 50 μL of the drug solution to prepare a second solution (concentration: 3.0 wt %). The first solution and the second solution were then blended at an equal volume (50 μL) to prepare a hydrogel. In this preparation, the molar ratio of the thiol groups to the maleimide groups was 1.0, and the pH of the blending solution was 6.0. By visual confirmation, the gelation was successful and took 2-3 minutes.

Example 28

Preparation of the Drug Delivery System (14)

0.1 g of Herceptin powder was dissolved in deionized water to form a drug solution (concentration: 190 mg/mL). Next, 0.001 g of polyglutamic acid (PGA) containing maleimide groups (Mw: 200-400 kDa, DS (grafting ratio): 11.3%) was dissolved in 50 μL of the drug solution to prepare a first solution (concentration: 2.0 wt %). Next, 0.001 g of polyethylene glycol (PEG) containing thiol groups (Mw: 5 kDa, 4-arm type) was dissolved in 50 μL of the drug solution to prepare a second solution (concentration: 2.0 wt %). The first solution and the second solution were then blended at an equal volume (50 μL) to prepare a hydrogel. In this preparation, the molar ratio of the thiol groups to the maleimide groups was 1.0, and the pH of the blending solution was 6.0. By visual confirmation, the gelation was successful and took 3-5 minutes.

Example 29

Preparation of the Drug Delivery System (15)

0.1 g of Herceptin powder was dissolved in deionized water to form a drug solution (concentration: 160 mg/mL). Next, 0.00075 g of polyglutamic acid (PGA) containing maleimide groups (Mw: 200-400 kDa, DS (grafting ratio): 19.8%) was dissolved in 50 μL of the drug solution to prepare a first solution (concentration: 1.5 wt %). Next, 0.0015 g of polyethylene glycol (PEG) containing thiol groups (Mw: 5 kDa, 4-arm type) was dissolved in 50 μL of the drug solution to prepare a second solution (concentration: 3.0 wt %). The first solution and the second solution were then blended at an equal volume (50 μL) to prepare a hydrogel. In this preparation, the molar ratio of the thiol groups to the maleimide groups was 1.0, and the pH of the blending solution was 6.0. By visual confirmation, the gelation was successful and took less than 2 minutes.

Example 30

Preparation of the Drug Delivery System (16)

0.01848 g of Herceptin powder in 50 uL MOPS buffer and 0.001 g of polyglutamic acid (PGA) containing maleimide groups (Mw: 200-400 kDa, DS (grafting ratio): 11.3%) in 50 uL MOPS buffer were blended to form a complex solution and centrifuged to remove the 30 uL supernatant. Next, 0.001 g of polyethylene glycol (PEG) containing thiol groups (Mw: 5 kDa, 4-arm type) was dissolved in 30 μL of 0.9% NaCl solution and blended with the complex solution to prepare a hydrogel (final drug concentration: 184.8 mg/mL). In this preparation, the molar ratio of the thiol groups to the maleimide groups was 1.0, and the pH of the blending solution was 6.0. By visual confirmation, the gelation was successful and took 5 minutes.

Example 31

Preparation of the Drug Delivery System (17)

A Herceptin/Zn complex solution having concentration of 128.0 mg/mL was prepared using 0.9% NaCl solution as a buffer solution. A proper amount of polyglutamic acid (PGA) containing maleimide groups (Mw: 1,000 kDa, DS (grafting ratio): 12.5%) and polyethylene glycol (PEG) containing thiol groups (Mw: 5 kDa, 4-arm type) were dissolved in the Herceptin/Zn complex solution to prepare Herceptin hydrogels with PGA concentration of 1.0 wt % and PEG concentration of 0.75 wt % (the molar ratio of the thiol groups to the maleimide groups was 0.7) under an acidic condition with a pH value of 5.0 to prepare a hydrogel. The gelation time was more than 30 minutes.

Example 32

Preparation of the Drug Delivery System (18)

A Herceptin/Zn complex solution having concentration of 208.0 mg/mL was prepared using 0.5M histidine solution as a buffer solution. A proper amount of polyglutamic acid (PGA) containing maleimide groups (Mw: 1,000 kDa, DS (grafting ratio): 12.5%) and polyethylene glycol (PEG) containing thiol groups (Mw: 5 kDa, 4-arm type) were dissolved in the Herceptin/Zn complex solution to prepare Herceptin hydrogels with PGA concentration of 1.3 wt % and PEG concentration of 0.8 wt % (the molar ratio of the thiol groups to the maleimide groups was 0.6) under an acidic condition with a pH value of 4.3 to prepare a hydrogel. The gelation time was 5-10 minutes.

Example 33

Preparation of the Drug Delivery System (19)

0.004 g of Doxorubicin powder was dissolved in deionized water to form a drug solution (concentration: 4.0 mg/mL). Next, 0.0015 g of polyglutamic acid (PGA) containing maleimide groups (Mw: 200-400 kDa, DS (grafting ratio): 11.5%) was dissolved in 50 μL of the drug solution to prepare a first solution (concentration: 3.0 wt %). Next, 0.0015 g of polyethylene glycol (PEG) containing thiol groups (Mw: 5 kDa, 4-arm type) was dissolved in 50 μL of the drug solution to prepare a second solution (concentration: 3.0 wt %). The first solution and the second solution were then blended at an equal volume (50 μL) to prepare a hydrogel. In this preparation, the molar ratio of the thiol groups to the maleimide groups was 1.0, and the pH of the blending solution was 4.5. By visual confirmation, the gelation was successful and took 20-30 minutes.

Comparative Example 1

Preparation of the Drug Delivery System 0.002 g of Doxorubicin powder was dissolved in deionized water to form a drug solution (concentration: 2.0 mg/mL). Next, 0.001 g of polyglutamic acid (PGA) containing maleimide groups (Mw: 200-400 kDa, DS (grafting ratio): 11.5%) was dissolved in 50 μL of the drug solution to prepare a first solution (concentration: 2.0 wt %). Next, 0.006 g of polyethylene glycol (PEG) containing thiol groups (Mw: 5 kDa, 4-arm type) was dissolved in 50 μL of the drug solution to prepare a second solution (concentration: 12 wt %). The first solution and the second solution were then blended at an equal volume (50 μL) to prepare a hydrogel. In this preparation, the molar ratio of the thiol groups to the maleimide groups was 6.0, and the pH of the blending solution was 5.0. By visual confirmation, the gelation is failed.

Example 34

Effect of pH on Preparation of the Hydrogels

Various solutions of polyglutamic acid (PGA) containing maleimide groups (Mw: 200-400 kDa, DS (grafting ratio): 11.5%) having a concentration of 1.5 wt % were prepared using various buffer solutions. Various solutions of polyethylene glycol (PEG) containing thiol groups (Mw: 5 kDa, 4-arm type) having a concentration of 1.5 wt % were prepared using various buffer solutions. The solution of polyglutamic acid (PGA) containing maleimide groups and the solution of polyethylene glycol (PEG) containing thiol groups were mixed under various pH environments to prepare hydrogels. The gelation processes were observed. The results, such as gelation time, homogeneity and hydrogel stiffness, are shown on Table 1.

TABLE 1

| | 1.5 wt % PGA-MA (Mw: 200-400 kDa, DS (grafting ratio): 11.5%) solution 1.5 wt% PEG-SH (Mw: 5 kDa, 4-arm type) solution | | | | | |
|---|---|---|---|---|---|---|
| Buffer solution | 0.05M carbonate buffer (pH9.6) | 0.5M PB buffer (pH7.4) | 10 × PBS (pH7.8) or 0.05M PB buffer (pH7.4) | 2 × PBS (pH7.8) | 1 × PBS (pH7.8) | 0.1M histidine buffer (pH4.0) |
| pH value (mixture) | 8.6 | 7.2 | 6.5 | 5.0 | 4.5 | 4.2 |
| Gelation time | immediately | immediately | ~30 sec | ~5 min | ~13 min | ~20 min |
| Homogeneity | very poor | poor | good | very good | very good | very good |
| Hydrogel stiffness | good | week | good | good | good | good |

In this example, under acidic pH environments (i.e. pH=4.2, 4.5, 5.0, and 6.5), appropriate gelation time and homogeneity of the mixture are obtained during the preparation. In addition, the formed hydrogel in such conditions possesses preferable stiffness.

Comparative Example 2

Effect of Alkaline pH on Encapsulation and Dissolution of the Drug-Loaded Hydrogels A Herceptin solution having a concentration of 50.0 mg/mL with a pH value of 7.8 was prepared. A proper amount of polyglutamic acid (PGA) containing maleimide groups (Mw: 1,000 kDa, DS (grafting ratio): 31.6%) was dissolved in the Herceptin solution to prepare a first solution having a concentration of 2.0 wt %. A proper amount of polyethylene glycol (PEG) containing thiol groups (Mw: 5 kDa, 4-arm type) was dissolved in the Herceptin solution to prepare a second solution having a concentration of 4.0 wt %. The first solution and the second solution were mixed (the molar ratio of the thiol groups to the maleimide groups was 0.72) under a pH value of 7.8 (an alkaline condition) to prepare a hydrogel (GAEG01). The gelation time was less than 2 minutes.

Next, a proper amount of polyglutamic acid (PGA) containing maleimide groups (Mw: 1,000 kDa, DS (grafting ratio): 31.6%) was dissolved in the Herceptin solution to prepare a first solution having a concentration of 2.0 wt %. A proper amount of polyethylene glycol (PEG) containing thiol groups (Mw: 10 kDa, 4-arm type) was dissolved in the Herceptin solution to prepare a second solution having a concentration of 4.0 wt %. The first solution and the second solution were mixed (the molar ratio of the thiol groups to the maleimide groups was 0.36) under a pH value of 7.8 (an alkaline condition) to prepare a hydrogel (GAEG02). Also, the gelation time was less than 2 minutes.

In this comparative example, the mixture of the first solution and the second solution was inhomogeneous during the preparation due to rapid gelation (less than 2 minutes). In tests of drug-release behavior, release of Herceptin from the hydrogels was incomplete. The hydrogels (GAEG01 and GAEG02) merely released Herceptin for about 28 days. In addition, in tests of drug structure and activity, the integrity of the molecular structure of Herceptin was seriously damaged (formation of numerous Herceptin fragments) and the activity thereof was lost (the binding ability to antigen was significantly reduced).

Example 35

Effect of Acidic pH on Encapsulation and Dissolution of the Drug-Loaded Hydrogels The hydrogel GAEG13 was prepared by Example 25. The hydrogel GAEG14 was prepared by Example 26. The hydrogel GAEG15 was prepared by Example 27. Effect of acidic pH on encapsulation and dissolution of the drug-loaded hydrogels (GAEG13, GAEG14 and GAEG15) was tested.

In this example, the maximum drug loading concentration of the hydrogels (GAEG13, GAEG14 and GAEG15) achieved 205 mg/mL. The mixture (hydrogel/drug) of the first solution and the second solution was homogeneous during the preparation due to sufficient gelation time (2-17 minutes). In tests of drug release behavior, release of Herceptin from the hydrogels was complete. The hydrogels (GAEG13, GAEG14 and GAEG15) released Herceptin for up to about 50 days (i.e. the hydrogels with sustained-release capacity). In addition, in tests of drug structure and activity, the integrity of the molecular structure of Herceptin was maintained, for example, to Day 35, there was still no Herceptin fragment formation. The biological activity thereof was thus maintained (the binding ability to antigen was still high).

Example 36

The Dissolution Effect of the Drug Complex-Loaded Hydrogel (1)

0.01848 g of Herceptin powder in 50 uL MOPS buffer and 0.001 g of polyglutamic acid (PGA) containing maleimide groups (Mw: 200-400 kDa, DS (grafting ratio): 11.3%) in 50 uL MOPS buffer were blended to form a complex solution and centrifuged to remove the 30 uL supernatant. Next, 0.001 g of polyethylene glycol (PEG) containing thiol groups (Mw: 5 kDa, 4-arm type) was dissolved in 30 μL of 0.9% NaCl solution and blended with the complex solution to prepare a hydrogel (PGA01) (final drug concentration: 184.8 mg/mL). In this preparation, the molar ratio of the thiol groups to the maleimide groups was 1.0, and the pH of the blending solution was 6.0. By visual confirmation, the gelation was successful and took 5 minutes.

In this example, in tests of drug release behavior, release of Herceptin from the hydrogel was complete. The hydrogel (PGA01) released Herceptin for up to about 42 days (i.e. the hydrogel with sustained-release capacity). In addition, in tests of drug structure and activity, the integrity of the molecular structure of Herceptin was maintained, for example, to Day 28, there was still no Herceptin fragment/aggregation formation. The biological activity thereof was thus maintained (the binding ability to antigen was still high).

Example 37

The Dissolution Effect of the Drug Complex-Loaded Hydrogels (2)

A Herceptin/Zn complex solution having concentration of 128.0 mg/mL was prepared using 0.9% NaCl solution as a buffer solution. A proper amount of polyglutamic acid (PGA) containing maleimide groups (Mw: 1,000 kDa, DS (grafting ratio): 12.5%) and polyethylene glycol (PEG) containing thiol groups (Mw: 5 kDa, 4-arm type) were dissolved in the Herceptin/Zn complex solution to prepare Herceptin hydrogels with PGA concentration of 1.0 wt % and PEG concentration of 0.75 wt % (the molar ratio of the thiol groups to the maleimide groups was 0.7) under a pH value of 5.0 (an acidic condition) to prepare a hydrogel (GAEGZ001). The gelation time was more than 30 minutes.

A Herceptin/Zn complex solution having concentration of 208.0 mg/mL was prepared using 0.5M histidine solution as a buffer solution. A proper amount of polyglutamic acid (PGA) containing maleimide groups (Mw: 1,000 kDa, DS (grafting ratio): 12.5%) and polyethylene glycol (PEG) containing thiol groups (Mw: 5 kDa, 4-arm type) were dissolved in the Herceptin/Zn complex solution to prepare Herceptin hydrogels with PGA concentration of 1.3 wt % and PEG concentration of 0.8 wt % (the molar ratio of the thiol groups to the maleimide groups was 0.6) under a pH value of 4.3 (an acidic condition) to prepare a hydrogel (GAEGZ002). The gelation time was 5-10 minutes.

In this example, the hydrogel (GAEGZ002) had a drug loading concentration of up to 208 mg/mL. The hydrogel (GAEGZ001) released Herceptin for up to about 42 days, and the hydrogel (GAEGZ002) released Herceptin for even up to about 70 days (i.e. the hydrogels with strong sustained-release capacity). It is because Herceptin and Zn interact to form a chelate, resulting in enhancement of the sustained-release effect. In addition, in tests of drug structure and activity, the integrity and stability of the molecular structure of Herceptin was maintained, for example, the monomer of released Herceptin was over 90%. The biological activity thereof was thus maintained (the binding ability to antigen was still high).

Example 38

The Release Behavior of the Drug-Loaded Hydrogels

A Herceptin solution having a concentration of 10.6 mg/mL was prepared using 0.9% NaCl solution as a buffer solution. A proper amount of polyglutamic acid (PGA) containing maleimide groups (Mw: 200-400 kDa, DS (grafting ratio): 11.3%) was then dissolved in the Herceptin solution to prepare a first solution having a concentration of 3.0 wt %. A proper amount of polyethylene glycol (PEG) containing thiol groups (Mw: 5 kDa, 4-arm type) was then dissolved in the Herceptin solution to prepare a second solution having a concentration of 3.0 wt %. The first solution and the second solution were then mixed (the molar ratio of the thiol groups to the maleimide groups was 1.0) under a pH value of 6.0 (an acidic condition) to prepare a hydrogel. The gelation time was 10-15 minutes.

A Herceptin solution having a concentration of 128.6 mg/mL was prepared using 0.9% NaCl solution as a buffer solution. A proper amount of polyglutamic acid (PGA) containing maleimide groups (Mw: 200-400 kDa, DS (grafting ratio): 11.3%) was then dissolved in the Herceptin solution to prepare a first solution having a concentration of 3.0 wt %. A proper amount of polyethylene glycol (PEG) containing thiol groups (Mw: 5 kDa, 4-arm type) was then dissolved in the Herceptin solution to prepare a second solution having a concentration of 3.0 wt %. The first solution and the second solution were then mixed (the molar ratio of the thiol groups to the maleimide groups was 1.0) under a pH value of 6.0 (an acidic condition) to prepare a hydrogel (GAEG11). The gelation time was 4 minutes.

A Herceptin solution having a concentration of 205.0 mg/mL was prepared using 0.9% NaCl solution as a buffer solution. A proper amount of polyglutamic acid (PGA) containing maleimide groups (Mw: 200-400 kDa, DS (grafting ratio): 11.3%) was then dissolved in the Herceptin solution to prepare a first solution having a concentration of 3.0 wt %. A proper amount of polyethylene glycol (PEG) containing thiol groups (Mw: 5 kDa, 4-arm type) was then dissolved in the Herceptin solution to prepare a second solution having a concentration of 3.0 wt %. The first solution and the second solution were then mixed (the molar ratio of the thiol groups to the maleimide groups was 1.0) under a pH value of 6.0 (an acidic condition) to prepare a hydrogel (GAEG15). The gelation time was 4 minutes.

In this example, in tests of drug release behavior, the results indicate that the higher the drug loading concentration, the longer the drug release period. When the drug loading concentration was 128.6 mg/mL or 205.0 mg/mL, the drug release period was up to about 42 days.

Example 39

The Release Behavior of the Drug Complex-Loaded Hydrogels

A Herceptin/Zn complex solution having concentration of 9.3 mg/mL was prepared using 0.5M histidine solution as a buffer solution. A proper amount of polyglutamic acid (PGA) containing maleimide groups (Mw: 200-400 kDa, DS (grafting ratio: 9.0%) and polyethylene glycol (PEG) containing thiol groups (Mw: 5 kDa, 4-arm type) were dissolved in the Herceptin/Zn complex solution to prepare Herceptin hydrogels with PGA concentration of 1.5 wt % and PEG concentration of 1.5 wt % (the molar ratio of the thiol groups to the maleimide groups was 1.0) under a pH value of 4.1 (an acidic condition) to prepare a hydrogel (GAEGZ007). The gelation time was 50-60 minutes.

A Herceptin/Zn complex solution having concentration of 93.0 mg/mL was prepared using 0.5M histidine solution as a buffer solution. A proper amount of polyglutamic acid (PGA) containing maleimide groups (Mw: 200-400 kDa, DS (grafting ratio: 9.0%) and polyethylene glycol (PEG) containing thiol groups (Mw: 5 kDa, 4-arm type) were dissolved in the Herceptin/Zn complex solution to prepare Herceptin hydrogels with a PGA concentration of 1.5 wt % and a PEG concentration of 1.5 wt % (the molar ratio of the thiol groups to the maleimide groups was 1.0) under a pH value of 4.2 (an acidic condition) to prepare a hydrogel (GAEGZ008). The gelation time was 35-40 minutes.

A Herceptin/Zn complex solution having concentration of 171.7 mg/mL was prepared using 0.5M histidine solution as a buffer solution. A proper amount of polyglutamic acid (PGA) containing maleimide groups (Mw: 200-400 kDa, DS (grafting ratio: 9.0%) and polyethylene glycol (PEG) containing thiol groups (Mw: 5 kDa, 4-arm type) were dissolved in the Herceptin/Zn complex solution to prepare Herceptin hydrogels with PGA concentration of 1.5 wt % and PEG concentration of 1.5 wt % (the molar ratio of the thiol groups to the maleimide groups was 1.0) under a pH value of 4.3 (an acidic condition) to prepare a hydrogel (GAEGZ009). The gelation time was 25-30 minutes. In this example, in tests of drug release behavior, the results indicate that the higher the drug loading concentration, the longer the drug release period. When the drug loading concentration was 93.0 mg/mL or 171.7 mg/mL, the drug release period was up to about 35 days.

Example 40

Effect of Acidic pH on Encapsulation and Dissolution of the Drug-Loaded Hydrogels An Etanercept solution having a concentration of 141.3 mg/mL was prepared. A proper amount of polyglutamic acid (PGA) containing maleimide groups (Mw: 200-400 kDa, DS (grafting ratio): 5.0%) was dissolved in the Etanercept solution to prepare a first solution having a concentration of 4.1 wt %. A proper amount of polyethylene glycol (PEG) containing thiol groups (Mw: 5 kDa, 4-arm type) was dissolved in the Etanercept solution to prepare a second solution having a concentration of 1.5 wt %. The first solution and the second solution were mixed (the molar ratio of the thiol groups to the maleimide groups was 0.8) under a pH value of 6.3 (an acidic condition) to prepare a hydrogel. The gelation time was 90-120 minutes.

Next, a proper amount of polyglutamic acid (PGA) containing maleimide groups (Mw: 200-400 kDa, DS (grafting ratio): 5.0%) was dissolved in the Etanercept solution to prepare a first solution having a concentration of 4.9 wt %. A proper amount of polyethylene glycol (PEG) containing thiol groups (Mw: 5 kDa, 4-arm type) was dissolved in the Etanercept solution to prepare a second solution having a concentration of 1.5 wt %. The first solution and the second solution were mixed (the molar ratio of the thiol groups to the maleimide groups was 0.67) under a pH value of 6.3 (an acidic condition) to prepare a hydrogel. The gelation time was 45-90 minutes.

Next, a proper amount of polyglutamic acid (PGA) containing maleimide groups (Mw: 200-400 kDa, DS (grafting ratio): 5.0%) was dissolved in the Etanercept solution to prepare a first solution having a concentration of 5.7 wt %. A proper amount of polyethylene glycol (PEG) containing thiol groups (Mw: 5 kDa, 4-arm type) was dissolved in the Etanercept solution to prepare a second solution having a concentration of 1.5 wt %. The first solution and the second solution were mixed (the molar ratio of the thiol groups to the maleimide groups was 0.57) under a pH value of 6.3 (an acidic condition) to prepare a hydrogel. The gelation time was 30-45 minutes.

Next, a proper amount of polyglutamic acid (PGA) containing maleimide groups (Mw: 200-400 kDa, DS (grafting ratio): 5.0%) was dissolved in the Etanercept solution to prepare a first solution having a concentration of 6.5 wt %. A proper amount of polyethylene glycol (PEG) containing thiol groups (Mw: 5 kDa, 4-arm type) was dissolved in the Etanercept solution to prepare a second solution having a concentration of 1.5 wt %. The first solution and the second solution were mixed (the molar ratio of the thiol groups to the maleimide groups was 0.5) under a pH value of 6.3 (an acidic condition) to prepare a hydrogel. The gelation time was 30-45 minutes.

In this example, the maximum drug loading concentration of the hydrogels achieved 141.3 mg/mL. The mixture (hydrogel/drug) of the first solution and the second solution was homogeneous during the preparation due to sufficient gelation time (30-120 minutes). In tests of drug release behavior, release of Etanercept from the hydrogels was complete. The hydrogels released Etanercept for up to about 30 days (i.e. the hydrogels with sustained-release capacity). In addition, in tests of drug structure and activity, the integrity of the molecular structure of Etanercept was maintained. The biological activity thereof was thus maintained (the binding ability to antigen was still high).

Example 41

Effect of Acidic pH on Encapsulation and Dissolution of the Drug-Loaded Hydrogels A HSA (human serum albumin) solution having a concentration of 100 mg/mL was prepared. A proper amount of polyglutamic acid (PGA) containing maleimide groups (Mw: 200-400 kDa, DS (grafting ratio): 12.1%) was dissolved in the HSA solution to prepare a first solution having a concentration of 2.0 wt %. A proper amount of polyethylene glycol (PEG) containing thiol groups (Mw: 5 kDa, 4-arm type) was dissolved in the HSA solution to prepare a second solution having a concentration of 2.0 wt %. The first solution and the second solution were mixed (the molar ratio of the thiol groups to the maleimide groups was 1.0) under a pH value of 5.0-6.15 (an acidic condition) to prepare a hydrogel (A). The gelation time was 8-12 minutes.

A HSA (human serum albumin) solution having a concentration of 200 mg/mL was prepared. Next, a proper amount of polyglutamic acid (PGA) containing maleimide groups (Mw: 200-400 kDa, DS (grafting ratio): 12.1%) was dissolved in the HSA solution to prepare a first solution having a concentration of 2.0 wt %. A proper amount of polyethylene glycol (PEG) containing thiol groups (Mw: 5 kDa, 4-arm type) was dissolved in the HSA solution to prepare a second solution having a concentration of 2.0 wt %. The first solution and the second solution were mixed (the molar ratio of the thiol groups to the maleimide groups was 1.0) under a pH value of 5.0-6.15 (an acidic condition) to prepare a hydrogel (B). The gelation time was 2.5-4.2 minutes.

A HSA (human serum albumin) solution having a concentration of 300 mg/mL was prepared. Next, a proper amount of polyglutamic acid (PGA) containing maleimide groups (Mw: 200-400 kDa, DS (grafting ratio): 12.1%) was dissolved in the HSA solution to prepare a first solution having a concentration of 2.0 wt %. A proper amount of polyethylene glycol (PEG) containing thiol groups (Mw: 5 kDa, 4-arm type) was dissolved in the HSA solution to prepare a second solution having a concentration of 2.0 wt %. The first solution and the second solution were mixed (the molar ratio of the thiol groups to the maleimide groups was 1.0) under a pH value of 6.15 (an acidic condition) to prepare a hydrogel (C). The gelation time was less than 1 minute.

In this example, the maximum drug loading concentration of the hydrogels (A, B and C) achieved 100-300 mg/mL. The mixture (hydrogel/drug) of the first solution and the second solution was homogeneous during the preparation due to sufficient gelation time. In addition, in tests of drug structure, the integrity and stability of the molecular structure of HSA was maintained, for example, the monomer of released HSA from the hydrogels (A, B and C) was respectively 94.1%, 92.8% and 92.6%.

Comparative Example 3

Effect of Alkaline pH on Encapsulation and Dissolution of the Drug-Loaded Hydrogels A HSA (human serum albumin) solution having a concentration of 50 mg/mL was prepared. A proper amount of polyglutamic acid (PGA) containing maleimide groups (Mw: 200-400 kDa, DS (grafting ratio): 12.1%) was dissolved in the HSA solution to prepare a first solution having a concentration of 2.0 wt %. A proper amount of polyethylene glycol (PEG) containing thiol groups (Mw: 5 kDa, 4-arm type) was dissolved in the HSA solution to prepare a second solution having a concentration of 2.0 wt %. The first solution and the second solution were mixed (the molar ratio of the thiol groups to the maleimide groups was 1.0) under a pH value of 8.18 (an alkaline condition) to prepare a hydrogel (D). However, the hydrogel was gelatinized immediately.

In this comparative example, the mixture of the first solution and the second solution was inhomogeneous during the preparation due to rapid gelation (i.e. the hydrogel was gelatinized immediately). In addition, in tests of drug structure, the integrity of the molecular structure of HSA was seriously damaged (formation of numerous HSA fragments). The monomer of released HSA from the hydrogel was merely 75.8%.

Example 42

Effect of Acidic pH on Encapsulation and Dissolution of the Drug-Loaded Hydrogels A Liraglutide solution having a concentration of 20 mg/mL was prepared. A proper amount of polyglutamic acid (PGA) containing maleimide groups (Mw: 200-400 kDa, DS (grafting ratio): 12.1%) was dissolved in the Liraglutide solution to prepare a first solution having a concentration of 2.0 wt %. A proper amount of polyethylene glycol (PEG) containing thiol groups (Mw: 5 kDa, 4-arm type) was dissolved in the Liraglutide solution to prepare a second solution having a concentration of 2.0 wt %. The first solution and the second solution were mixed (the molar ratio of the thiol groups to the maleimide groups was 1.0) under a pH value of 5.0 (an acidic condition) to prepare a hydrogel (A). The gelation time was 8-12 minutes.

A Liraglutide solution having a concentration of 20 mg/mL was prepared. Next, a proper amount of polyglutamic acid (PGA) containing maleimide groups (Mw: 300 kDa, DS (grafting ratio): 12.1%) was dissolved in the Liraglutide solution to prepare a first solution having a concentration of 3.0 wt %. A proper amount of polyethylene glycol (PEG) containing thiol groups (Mw: 5 kDa, 4-arm type) was dissolved in the Liraglutide solution to prepare a second solution having a concentration of 3.0 wt %. The first solution and the second solution were mixed (the molar ratio of the thiol groups to the maleimide groups was 1.0) under a pH value of 5.0 (an acidic condition) to prepare a hydrogel (B). The gelation time was 2.5-4.2 minutes.

In this example, the mixture (hydrogel/drug) of the first solution and the second solution was homogeneous during the preparation due to sufficient gelation time (2-12 minutes). In addition, in tests of drug structure, the integrity and stability of the molecular structure of Liraglutide was maintained, for example, the monomer of released Liraglutide from the hydrogels (A and B) was 100%.

Example 43

The In-Vivo Pharmacokinetics (PK) Study of the Drug-Loaded Hydrogel

A "Herceptin" solution having a concentration of 20.0 mg/mL was first prepared as a control group.

Another Herceptin solution having concentration of 20.0 mg/mL was prepared. Next, a proper amount of polyglutamic acid (PGA) containing maleimide groups (Mw: 200-400 kDa, DS (grafting ratio): 11.4%) was dissolved in the Herceptin solution to prepare a first solution having a concentration of 3.0 wt %. A proper amount of polyethylene glycol (PEG) containing thiol groups (Mw: 5 kDa, 4-arm type) was then dissolved in the Herceptin solution to prepare a second solution having a concentration of 3.0 wt %. The first solution and the second solution were then mixed (the molar ratio of the thiol groups to the maleimide groups was 1.0) under a pH value of 6.0 (an acidic condition) to prepare a "Herceptin-loaded hydrogel" as an experimental group.

Pharmacokinetics (PK) experiments were carried out with "Herceptin" (control group) and "Herceptin-loaded hydrogel" (experimental group) in rats. The dose thereof was 50 mg/kg. The drug concentration in plasma was respectively measured on day 7, day 14, day 21, day 28, and day 35 after dosing to build serum concentration-time profiles. In accordance with the data of the serum concentration-time profiles, pharmacokinetics parameters, such as $T_{max}$, $C_{max}$, $T_{1/2}$, $AUC_{D35}$ and BA (bioavailability), were obtained and are shown in Table 2.

TABLE 2

| Pharmacokinetics (PK) parameters | | Herceptin | Herceptin-loaded hydrogel |
|---|---|---|---|
| $T_{max}$ | day | 3.0 ± 0 | 6.7 ± 0.6 |
| $C_{max}$ | µg/mL | 272 ± 25 | 154 ± 18 |
| $T_{1/2}$ | day | 2.6 ± 0.4 | 7 ± 3.7 |
| $AUC_{D35}$ | day * µg/mL | 3,079 ± 100 | 2,522 ± 215 |
| BA | % | 100% | 82% |

The results indicate that, for the Herceptin-loaded hydrogel, $C_{max}$ thereof is about 60% of the original Herceptin, $T_{max}$ thereof delayed 2 times, and $T_{1/2}$ thereof extended 2.7 times. Therefore, the Herceptin-loaded hydrogel possesses sustained-release capacity.

Example 44

The In-Vivo Pharmacokinetics (PK) Study of the Drug Complex-Loaded Hydrogel

A "Herceptin" solution having a concentration of 20.0 mg/mL was first prepared as a control group.

A Herceptin/Zn complex solution having concentration of 20.0 mg/mL was prepared using 0.9% NaCl solution as a solution. A proper amount of polyglutamic acid (PGA) containing maleimide groups (Mw: 200-400 kDa, DS (grafting ratio: 11.4%) and polyethylene glycol (PEG) containing thiol groups (Mw: 5 kDa, 4-arm type) were dissolved in the Herceptin/Zn complex solution with PGA concentration of 1.5 wt % and PEG concentration of 1.5 wt % (the molar ratio of the thiol groups to the maleimide groups was 1.0) under a pH value of 5.8 (an acidic condition) to prepare a "Herceptin/Zn complex-loaded hydrogel (Her/Zn-hydrogel)" as an experimental group. The gelation time was 40-50 minutes.

Pharmacokinetics (PK) experiments were carried out with "Herceptin" (control group) and "Herceptin/Zn complex-loaded hydrogel (Her/Zn-hydrogel)" (experimental group) in rats. The dose thereof was 50 mg/kg. The drug concentration in plasma was respectively measured on day 7, day 14, day 21, day 28, and day 35 after dosing to build serum concentration-time profiles. In accordance with the data of the serum concentration-time profiles, pharmacokinetics parameters, such as $T_{max}$, $C_{max}$, $T_{1/2}$, $AUC_{D35}$ and BA (bioavailability), were obtained and are shown in Table 3 and FIG. 1.

TABLE 3

| Pharmacokinetics (PK) parameters | | Herceptin | Herceptin/Zn complex-loaded hydrogel |
|---|---|---|---|
| $T_{max}$ | day | 3.0 ± 0 | 10 ± 3.5 |
| $C_{max}$ | µg/mL | 272 ± 25 | 76 ± 17 |
| $T_{1/2}$ | day | 2.6 ± 0.4 | 11 ± 12 |
| $AUC_{D35}$ | day * µg/mL | 3,079 ± 100 | 1,128 ± 448 |
| BA | % | 100% | 37% |

The results indicate that, for the Herceptin/Zn complex-loaded hydrogel, $C_{max}$ thereof is about 30% of the original Herceptin, $T_{max}$ thereof delayed 3 times, and $T_{1/2}$ thereof extended 4.2 times. Therefore, the Herceptin/Zn complex-loaded hydrogel possesses sustained-release capacity.

Example 45

The In-Vivo Pharmacodynamics (PD) Study of the Drug-Loaded Hydrogel

A "Dulbecco's phosphate-buffered saline (DPBS)" solution was provided as a control group.

A "Herceptin" solution having a concentration of 10 mg/mL was prepared as a first experimental group.

Another Herceptin solution having a concentration of 10 mg/mL was prepared. Next, a proper amount of polyglutamic acid (PGA) containing maleimide groups (Mw: 200-400 kDa, DS (grafting ratio): 11.5%) was dissolved in the Herceptin solution to prepare a first solution having a concentration of 3.0 wt %. A proper amount of polyethylene glycol (PEG) containing thiol groups (Mw: 5 kDa, 4-arm type) was then dissolved in the Herceptin solution to prepare a second solution having a concentration of 3.0 wt %. The first solution and the second solution were then mixed (the molar ratio of the thiol groups to the maleimide groups was 1.0) under a pH value of 6.0 (an acidic condition) to prepare a "Herceptin-loaded hydrogel" as a second experimental group.

Pharmacodynamics (PD) experiments were carried out with "DPBS" (control group), "Herceptin" (first experimental group), and "Herceptin-loaded hydrogel" (second experimental group) in BT474 breast cancer mouse. The dose of "Herceptin" and "Herceptin-loaded hydrogel" was 50 mg/kg. The tumor volume (mm$^3$) was respectively measured on specific days after dosing to build tumor-volume variation curves. In accordance with the data of the tumor-volume variation curves, the tumor growth inhibition (TGI) was calculated and is shown in Table 4.

TABLE 4

| Day 28 after dosing | TGI (% ± SEM) | BW (% ± SEM) | N |
|---|---|---|---|
| DPBS | 0.0 | 107.1 ± 1.6 | 8 |
| Herceptin | 52.7 ± 22.2 | 100.6 ± 4.1 | 7 |
| Herceptin-loaded hydrogel | 44.2 ± 32.0 | 102.5 ± 3.1 | 8 |

The results of tumor volume variation on Day 28 after dosing indicate that, compared to DPBS, Herceptin (dose: 50 mg/kg) applied by subcutaneous injection is able to inhibit tumor growth, and the TGI thereof was calculated as 52.7%.

The TGI of the Herceptin-loaded hydrogel is similar to that of Herceptin on Day 28 after dosing.

There was no significant change in body weight (BW) of the mouse during the experiments.

Example 46

The In-Vivo Pharmacodynamics (PD) Study of the Drug Complex-Loaded Hydrogel

A "Dulbecco's phosphate-buffered saline (DPBS)" solution was provided as a control group.

A Herceptin/Zn complex solution having concentration of 10.0 mg/mL was prepared using 0.9% NaCl solution as a solution. A proper amount of polyglutamic acid (PGA) containing maleimide groups (Mw: 200-400 kDa, DS (grafting ratio: 11.5%) and polyethylene glycol (PEG) containing thiol groups (Mw: 5 kDa, 4-arm type) were dissolved in the Herceptin/Zn complex solution with PGA concentration of 1.5 wt % and PEG concentration of 1.5 wt % (the molar ratio of the thiol groups to the maleimide groups was 1.0) under a pH value of 5.9 (an acidic condition) to prepare a "Herceptin/Zn complex-loaded hydrogel (Her/Zn-hydrogel)" as an experimental group. The gelation time was around 40 minutes.

Figure 2:
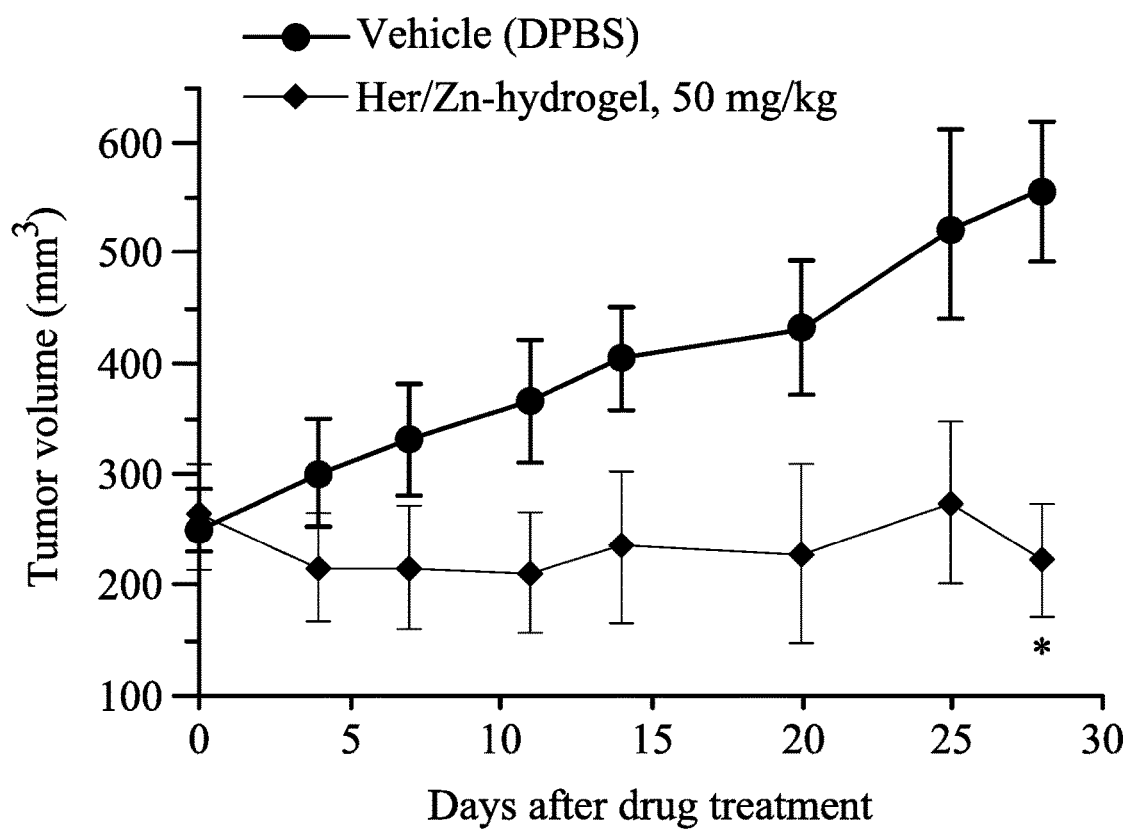
FIG. 2 is a figure showing the tumor-volume variation curves according to an embodiment of the disclosure.

Pharmacodynamics (PD) experiments were carried out with "DPBS" (control group) and "Herceptin/Zn complex-loaded hydrogel (Her/Zn-hydrogel)" (experimental group) in BT474 breast cancer mouse. The dose of "Herceptin/Zn-hydrogel" was 50 mg/kg. The tumor volume (mm$^3$) was respectively measured on specific days after dosing to build tumor-volume variation curves. In accordance with the data of the tumor-volume variation curves, the tumor growth inhibition (TGI) was calculated and is shown in Table 5 and FIG. 2.

TABLE 5

| Day 28 after dosing | TGI (% ± SEM) | BW (% ± SEM) | N |
|---|---|---|---|
| DPBS | 0.0 | 107.1 ± 1.6 | 8 |
| Her/Zn-hydrogel | 121.9 ± 35.0 | 98.8 ± 2.9 | 7 |

The results of tumor volume variation on Day 28 after dosing indicate that the Herceptin/Zn complex-loaded hydrogel is able to significantly inhibit tumor growth, and the TGI thereof was calculated as 121.9%.

There was no significant change in body weight (BW) of the mouse during the experiments.

The present disclosure provides a novel hydrogel composition which comprises polyglutamic acid (PGA) containing maleimide (MA) groups, and polyethylene glycol (PEG) containing thiol (SH) groups. Specifically, the hydrogel composition has an acidic pH value ranging from about 4.0 to about 6.5. The hydrogel can be applied in drug delivery systems. The hydrogel has the ability to carry high-dose drugs, with a maximum drug loading concentration up to about 300 mg/mL. The hydrogel is able to regulate the release behavior of drugs, for example, the sustained-release period is up to at least 35 days in vitro. Specifically, for drug complex-loaded hydrogels, $C_{max}$ thereof is about 30% of the drug uncovered by the hydrogel, $T_{max}$ thereof delayed 3 times, and $T_{1/2}$ thereof extended 4.2 times in vivo. The integrity and stability of the molecular structure and biological activity of drugs are maintained by the hydrogel. In addition, the hydrogel is able to encapsulate multivariate drugs, for example, macro-molecular drugs such as antibodies or proteins or peptides, or_hydrophilic or hydrophobic small molecules.

It will be apparent to those skilled in the art that various modifications and variations can be made to the disclosed embodiments. It is intended that the specification and examples be considered as exemplary only, with the true scope of the disclosure being indicated by the following claims and their equivalents.

What is claimed is:

1. A hydrogel composition, comprising:
   polyglutamic acid (PGA) containing maleimide groups; and
   polyethylene glycol (PEG) containing terminal thiol groups,
   wherein the hydrogel composition has a gelation pH value ranging from 4.0 to 6.5.

2. The hydrogel composition as claimed in claim 1, wherein the polyglutamic acid (PGA) containing maleimide groups has a molecular weight ranging from 10 kDa to 1,000 kDa.

3. The hydrogel composition as claimed in claim 1, wherein the polyglutamic acid (PGA) containing maleimide groups has a grafting ratio ranging from 5% to 40%.

4. The hydrogel composition as claimed in claim 1, wherein the polyglutamic acid (PGA) containing maleimide groups has a concentration ranging from 0.75 wt % to 10 wt % in the hydrogel composition.

5. The hydrogel composition as claimed in claim 1, wherein the polyglutamic acid (PGA) containing maleimide groups is free of thiol groups.

6. The hydrogel composition as claimed in claim 1, wherein the polyethylene glycol (PEG) containing terminal thiol groups has a molecular weight ranging from 2 kDa to 20 kDa.

7. The hydrogel composition as claimed in claim 1, wherein the polyethylene glycol (PEG) containing terminal thiol groups has a concentration ranging from 0.75 wt % to 10 wt % in the hydrogel composition.

8. The hydrogel composition as claimed in claim 1, wherein the polyethylene glycol (PEG) containing terminal thiol groups is 4-arm type, 8-arm type or Y-shape.

9. The hydrogel composition as claimed in claim 1, wherein the polyethylene glycol (PEG) containing terminal thiol groups is free of maleimide groups.

10. The hydrogel composition as claimed in claim 1, wherein the polyethylene glycol (PEG) containing terminal thiol groups and the polyglutamic acid (PGA) containing maleimide groups have a molar ratio of the thiol group to the maleimide group ranging from 0.2 to 5.0.

11. The hydrogel composition as claimed in claim 1, wherein the polyethylene glycol (PEG) containing terminal thiol groups and the polyglutamic acid (PGA) containing maleimide groups have a molar ratio of the thiol group to the maleimide group ranging from 1.0 to 1.5.

12. A drug delivery system, comprising:
    a hydrogel composition as claimed in claim 1; and
    a pharmaceutically active ingredient encapsulated in the hydrogel composition.

13. The drug delivery system as claimed in claim 12, wherein the pharmaceutically active ingredient is selected from the group consisting of growth factors, hormones, peptides, proteins, antibodies, hydrophilic small molecules and hydrophobic small molecules.

14. The drug delivery system as claimed in claim 13, wherein the pharmaceutically active ingredient is selected from the group consisting of intact antibodies and antibody fragments.

15. The drug delivery system as claimed in claim 13, wherein the pharmaceutically active ingredient is selected from the group consisting of murine antibodies, chimeric antibodies, humanized antibodies, and human antibodies.

16. The drug delivery system as claimed in claim 13, wherein the pharmaceutically active ingredient is selected from the group consisting of antineoplastic agents, antipsychotics, analgesics and antibiotics.

17. The drug delivery system as claimed in claim 12, wherein the pharmaceutically active ingredient is further associated with a polymer, metal, charged compounds or charged particles to form a complex thereof.

18. The drug delivery system as claimed in claim 17, wherein the polymer comprises polyglutamic acid (PGA), hyaluronic acid, chitosan or dextran.

19. The drug delivery system as claimed in claim 17, wherein the metal comprises zinc, calcium, magnesium or iron.

20. The drug delivery system as claimed in claim 17, wherein the complex has a size ranging from 10 nm to 100 μm.

21. The drug delivery system as claimed in claim 17, wherein the pharmaceutically active ingredient or the complex has a concentration ranging from 1 mg/mL to 300 mg/mL.

* * * * *